United States Patent
Wodlinger et al.

(10) Patent No.: US 11,451,203 B2
(45) Date of Patent: Sep. 20, 2022

(54) ISOLATION AMPLIFICATION CIRCUIT WITH IMPROVED COMMON MODE REJECTION

(71) Applicant: CathVision ApS, København N (DK)

(72) Inventors: Harold Wodlinger, Toronto (CA); Arkadiusz Biel, Toronto (CA); Hogyu Xi, Mississauga (CA); Richard Fine, Mississauga (CA)

(73) Assignee: CathVision ApS, København N (DK)

( * ) Notice: Subject to any disclaimer, the term of this patent is extended or adjusted under 35 U.S.C. 154(b) by 0 days.

(21) Appl. No.: 17/051,464

(22) PCT Filed: Apr. 25, 2019

(86) PCT No.: PCT/EP2019/060584
§ 371 (c)(1),
(2) Date: Oct. 29, 2020

(87) PCT Pub. No.: WO2019/211156
PCT Pub. Date: Nov. 7, 2019

(65) Prior Publication Data
US 2021/0058047 A1 Feb. 25, 2021

(30) Foreign Application Priority Data
Apr. 30, 2018 (EP) .................................... 18170084

(51) Int. Cl.
*H03F 3/45* (2006.01)
*A61B 5/301* (2021.01)
(Continued)

(52) U.S. Cl.
CPC .......... *H03F 3/45932* (2013.01); *A61B 5/301* (2021.01); *A61B 5/7203* (2013.01);
(Continued)

(58) Field of Classification Search
CPC .......... H03F 3/45932; H03F 1/26; H03F 1/34; H03F 2203/45084; H03F 2203/45548;
(Continued)

(56) References Cited

U.S. PATENT DOCUMENTS

2009/0018429 A1* 1/2009 Saliga .................. A61B 5/7221
600/407
2014/0336473 A1 11/2014 Greco
2015/0313501 A1 11/2015 Shachar

FOREIGN PATENT DOCUMENTS

EP 0570101 A2 11/1993
WO 2015026988 A1 2/2015

OTHER PUBLICATIONS

International Search Report and Written Opinion in International Patent Application No. PCT/EP2019/060584, dated May 24, 2019 (8 pages).

* cited by examiner

*Primary Examiner* — Khanh V Nguyen
*Assistant Examiner* — Khiem D Nguyen
(74) *Attorney, Agent, or Firm* — Nixon Peabody LLP

(57) ABSTRACT

An isolation amplification circuit having an input stage circuitry and a control circuitry stage interconnected through a galvanic isolation barrier. The input stage circuitry includes a first filter network and a second filter network for supplying first and second output signals in response to the application of first and second electrical input signals. The input stage circuitry includes a first feedback path configured for applying a first feedback signal to a common node of the first filter network to close a first feedback loop around the first filter network and a second feedback path configured for applying a second feedback signal to a common
(Continued)

node of the second filter network to close a second feedback loop around the second filter network.

14 Claims, 4 Drawing Sheets

(51) Int. Cl.
    *A61B 5/00*          (2006.01)
    *H03F 1/26*          (2006.01)
    *H03F 1/34*          (2006.01)
    *H03H 7/01*          (2006.01)
    *H03H 7/075*         (2006.01)
    *H03H 17/06*         (2006.01)
    *H03H 17/02*         (2006.01)

(52) U.S. Cl.
    CPC ................ *H03F 1/26* (2013.01); *H03F 1/34* (2013.01); *H03H 7/0138* (2013.01); *H03H 7/075* (2013.01); *H03H 17/06* (2013.01); *H03F 2203/45084* (2013.01); *H03F 2203/45548* (2013.01); *H03F 2203/45552* (2013.01); *H03F 2203/45568* (2013.01); *H03F 2203/45594* (2013.01); *H03H 2017/0298* (2013.01)

(58) Field of Classification Search
    CPC . H03F 2203/45552; H03F 2203/45568; H03F 2203/45594; A61B 5/301; A61B 5/7203; H03H 7/0138; H03H 7/075; H03H 17/06; H03H 2017/0298
    USPC ........................ 330/258, 254, 10, 9, 69, 284
    See application file for complete search history.

ISOLATION AMPLIFICATION CIRCUIT WITH IMPROVED COMMON MODE REJECTION

CROSS-REFERENCE TO RELATED APPLICATIONS

This application is a U.S. National Stage of International Application No. PCT/EP2019/060584, filed Apr. 25, 2019, which claims the benefit of European Patent Application No. 18170084.0, filed Apr. 30, 2018, both of which are incorporated herein by reference in their entireties.

The present invention relates to an isolation amplification circuit which comprises an input stage circuitry and a control circuitry stage interconnected through a galvanic isolation barrier. The input stage circuitry comprises a first filter network and a second filter network for supplying first and second output signals in response to the application of first and second electrical input signals. The input stage circuitry comprises a first feedback path configured for applying a first feedback signal to a common node of the first filter network to close a first feedback loop around the first filter network and a second feedback path configured for applying a second feedback signal to a common node of the second filter network to close a second feedback loop around the second filter network.

BACKGROUND OF THE INVENTION

Isolation amplifiers are a form of differential amplifier that allow measurement of small signals in the presence of a high common mode voltage by providing electrical isolation and an electrical/safety barrier, i.e. galvanic isolation. Isolation amplifiers are used in numerous applications and may for example be utilized to protect data acquisition components and systems from harmful common mode voltages. Common mode voltages are electrical potential differences between instrument (earth) ground and signal ground. Isolation amplifiers are for example used in harsh industrial environments, military applications, transportation, medical systems etc.

The ability of a differential amplifier to reject common mode voltage is specified by its so-called Common Mode Rejection Ratio (CMRR). Practical isolation amplifiers have certain limitations on their ability to reject common mode voltage due to various non-ideal characteristics of the differential amplifier and possibly unmatched impedances of input networks connected to respective inputs of the differential amplifier. Isolation amplifiers are for example often used with protective resistors and/or with respective input filter networks coupled in series with the inverting and non-inverting inputs of the differential amplifier. The role of these protective resistors and input filter networks is to remove unwanted frequency components or electrical noise from the inputs of the differential amplifier. Unfortunately, these resistors and input filter networks degrade the inherent CMRR of the differential amplifier and hence degrade the ability of the isolation amplifier to reject common mode noise or common mode voltage such as mains ripple voltage.

Medical isolation amplifiers are one specific type of isolation amplifier. Medical isolation amplifiers must isolate the patient from any possible contact with earth ground or mains/line voltage. In addition, the amount of current that may pass through the patient, i.e. leakage current, if the patient is accidentally connected to earth ground or mains/line voltage must be restricted to extremely small values. Techniques for accomplishing this include magnetic and optical isolation, and these techniques are well known in the art.

US 2014/0336473 A1 discloses isolation amplification circuit for medical applications. The isolation amplification circuit comprises an input stage circuitry and a control circuitry stage inter-connected through an electrical isolation barrier. The input stage circuitry of a single input channel comprises a differential amplifier with a feedback path connected from an output node of the differential amplifier to an internal node of the differential amplifier. The feedback path comprises an active lowpass filter and serves to provide DC-correction around the differential amplifier.

Hence, there remains a need in the art for isolation amplifiers with improved CMRR in particular isolation amplifiers, which can suppress the negative side effects of unmatched impedances of the input resistances or the input filter networks.

SUMMARY OF THE INVENTION

A first aspect of the invention relates to an isolation amplification circuit comprising: an input stage circuitry and a control circuitry stage inter-connected through a galvanic isolation barrier. The input stage circuitry is referenced to a first ground potential and configured to receive at least a first electrical signal and a second electrical signal generated by a signal source. The input stage circuitry comprises:

a first filter network comprising a first input node, a first output node and first common node wherein the first output node is configured to supply a first output signal in response to application of the first electrical signal at the first input node. The input stage circuitry further comprises a second filter network comprising a second input node, a second output node and a second common node, wherein the second output node is configured to supply a second output signal in response to application of the second electrical signal at the second input node. The input stage circuitry additionally comprises a first feedback path configured for lowpass filtering the first output signal and supplying a first lowpass filtered output signal to the first common node; and a second feedback path configured for lowpass filtering the second output signal and supplying a second lowpass filtered output signal to the second common node.

Each of the first filter network and second filter network may comprise at least one of a lowpass filter, highpass filter, bandpass filter and band-reject filter. Each of the first filter network and second filter network may comprise a plurality of interconnected passive components such as resistors, inductors and capacitors to form a transfer function of each of the first and second filter networks.

The skilled person will understand that the input stage circuitry may comprise one or more filter network(s) with respective lowpass filtered feedback paths in addition to the first and second filter networks to provide additional input channel(s) of the isolation amplification circuit.

The signal source may comprise a human or animal body in medically adapted embodiments of the isolation amplification circuit. The human or animal body may supply the first electrical signal as a first electro-physiological signal to the first input node of the first filter network via a first electrode and supply the second electrical signal as a second electro-physiological signal to the second input node of the second filter network via a second electrode. The first and second electrodes may be attached to the skin of the human with a suitable adhesive agent.

The lowpass filtering of the first feedback path may carried out by a first analog lowpass filter and/or by a first digital lowpass filter and the lowpass filtering of the second feedback path may likewise be carried out by a second analog lowpass filter and/or by a second digital lowpass filter. In one embodiment utilizing analog lowpass filters, the first feedback path comprises a first buffer amplifier and a first lowpass filter wherein the first buffer amplifier is connected between the first output node and an input of the first lowpass filter; and the second feedback path comprises a second buffer amplifier and second lowpass filter wherein the second buffer amplifier being connected between the second output node and an input of the second lowpass filter. Each of the first and second buffer amplifiers may comprise an operational amplifier for example coupled in unity gain mode via suitable feedback arrangement.

In one embodiment of the first and second filter networks, the first lowpass filter comprises a first feedback capacitor connected from the first common node to the first ground potential and a first feedback resistor connected between the first common node and an output of the first buffer amplifier; The second lowpass filter may comprises a second feedback capacitor connected from the second common node to the first ground potential and a second feedback resistor connected between the second common node and an output of the second buffer amplifier. Hence, a lowpass corner or cut-off frequency of the first lowpass filter is determined by the resistance and capacitance of the first feedback capacitor and first feedback resistor and a lowpass corner or cut-off frequency of the second lowpass filter is determined by the resistance and capacitance of the second feedback capacitor and second feedback resistor. The cut-off frequency of the first lowpass filter of the first feedback path may lie between 200 Hz and 2 kHz such as between 500 Hz and 1.5 kHz and a cut-off frequency of the second lowpass filter of the second feedback path may lie between 200 Hz and 2 kHz such as between 500 Hz and 1.5 kHz. The capacitance of the first feedback capacitor may be between 10 nF and 100 nF and the resistance of the first feedback resistor may be between 3 k$\Omega$ and 30 k$\Omega$. The the second feedback capacitor and second feedback resistor may be nominally identical to the first feedback capacitor and first feedback resistor, respectively.

According to one embodiment of the input stage circuitry, which incorporates first and second digital lowpass filters, the first feedback path comprises a first analog-to-digital converter, a first digital lowpass filter and a first digital-to-analog converter connected, e.g. in series, between the first output node and the first common node. The second feedback path likewise comprises a second analog-to-digital converter, a second digital lowpass filter and a second digital-to-analog converter connected, e.g. in series, between the second output node and the second common node.

Each of the first and second analog or digital lowpass filters may comprise a first order frequency response characteristic, i.e. a single pole, or a higher order frequency response characteristic. Generally, higher order frequency response characteristics, such as second order or third order, tend to improve the CMRR performance of the isolation amplification circuit albeit at the expense of higher complexity.

At least the first digital lowpass filter and the second digital lowpass filter are preferably integrated on a common or shared digital signal processor (DSP) circuit such as a software programmable DSP or a hard-wired DSP e.g. comprising an ASIC or a suitably configured FPGA. The software programmable DSP may form part of a microprocessor.

The input stage circuitry may form part of a single input channel of the isolation amplification circuit and connected to a single signal source which generates the first and second electrical signals.

The input stage circuitry may comprise a differential amplifier wherein an inverting input of the differential amplifier is electrically coupled to the first output signal of the first filter network and a non-inverting input of the differential amplifier is electrically coupled to the second output signal of the second filter network to produce an amplified output signal. The amplified output signal may be coupled to the control circuitry stage through the galvanic isolation barrier.

The skilled person will understand that corresponding components of the first and second filter networks preferably are nominally identical or matching. For example are passive components of the first filter network nominally identical to the corresponding passive components of the second filter network, e.g. exhibiting nominally identical resistances, capacitances or inductances, as the case may be. The skilled person will understand that such nominally matching components in a practical circuit construction will possess slightly different resistance, capacitance or inductance values due to manufacturing tolerances, drift ageing etc. These component mismatches lead to the previously-discussed discussed problems with impaired CMRR performance in prior art isolation amplification circuits.

The control circuitry stage of the isolation amplification may be connected to a power supply. The power supply may be connectable to a mains line which comprises at least one voltage phase, e.g. 120V/60 Hz, 230V/50 Hz or a local voltage and frequency, and earth ground.

Each of the first and second filter networks may additionally comprise at least one non-linear element(s) such as a transient-voltage-suppression (TVS) diode(s) or similar non-linear voltage limiters to protect each of the first and second filter networks and other circuits and components of the isolation amplification circuit against harmful transient voltages for example defibrillation associated voltage pulses/spikes as discussed in additional detail below with reference to the appended drawing material.

The galvanic isolation barrier may comprise one or more optical isolation element(s) and/or one or more magnetic isolation elements, such as a transformer, discussed in additional detail below with reference to the appended drawing material.

A second aspect of the invention relates to a method of suppressing common mode signals of an isolation amplification circuit, wherein said method comprises steps of:

a) applying a first electrical signal to a first input node of a first filter network of an input stage circuitry of the isolation amplification circuit, b) applying a second electrical signal to a second input node of a second filter network of the input stage circuitry, c) generating a first output signal of the first filter network in response to the first electrical signal, d) generating a second output signal of the second filter network in response to the second electrical signal, e) lowpass filtering the first output signal to generate a first feedback signal, f) lowpass filtering the second output signal to generate a second feedback signal, g) applying the first feedback signal to a common node of the first filter network to close a first feedback loop around the first filter network; and h) applying the second feedback signal to a common node of the second filter network to close a second feedback loop around the second filter network.

BRIEF DESCRIPTION OF THE DRAWINGS

Embodiments of the invention are described in more detail below with reference to the appended drawings, in which.

DESCRIPTION OF PREFERRED EMBODIMENTS

Figure 1A:
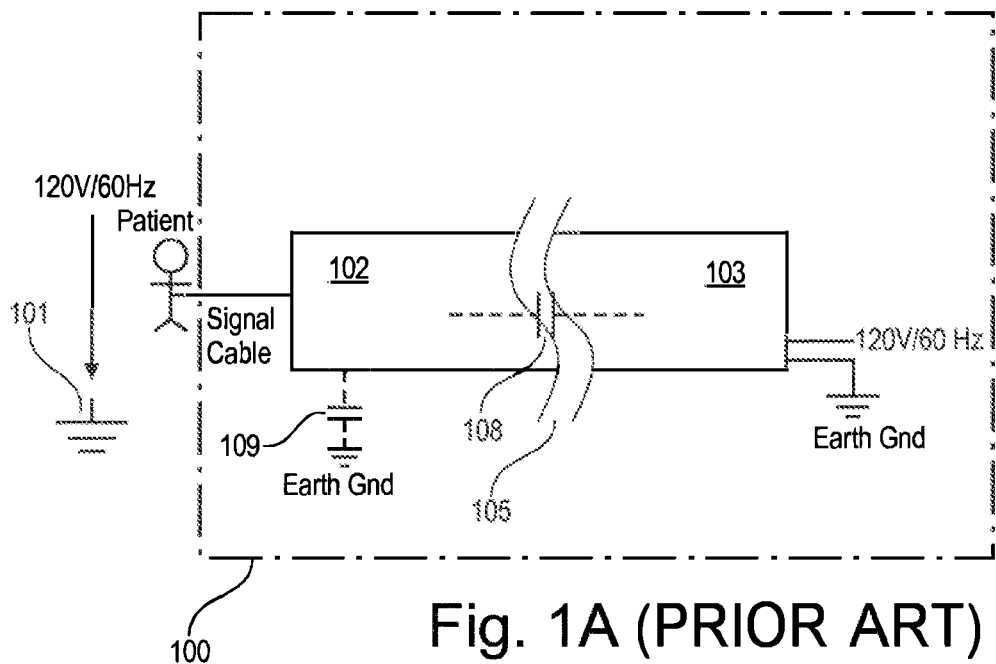
FIG. 1A shows a simplified schematic block diagram of a medical isolation amplification circuit connected to a patient via a signal cable.

In the following, various exemplary embodiments of an isolation amplification circuit are described and discussed with reference to the appended drawings. The skilled person will understand that even though the isolation amplification circuit is described in the context of medical applications, other applications of the isolation amplification circuit are envisioned such as harsh industrial environments, military applications, transportation etc. The skilled person will understand that the appended drawings are schematic and simplified for clarity and therefore merely show details which are essential to the understanding of the invention, while other details have been left out. Like reference numerals refer to like elements or components throughout. Like elements or components will therefore not necessarily be described in detail with respect to each figure. The skilled person will further appreciate that certain actions and/or steps may be described or depicted in a particular order of occurrence while those skilled in the art will understand that such specificity with respect to sequence is not actually required.

FIG. 1A shows a simplified schematic block diagram of an exemplary prior art medical isolation amplification circuit 100 connected to a patient via a signal cable for the purpose of explaining the background of the present invention. The medical isolation amplification circuit 100 is designed to isolate the patient from any possible contact with earth ground or the line voltage e.g. 120 V/60 Hz. In addition, the amount of current, i.e. leakage current, that may pass through the patient when that patient is accidentally connected to earth ground or line voltage must be restricted to extremely small values. The medical device standard requires that less than 50 uA flow into the patient under single fault conditions. Series resistors R1 and R2 and the isolation barrier 105 provide that protection. Techniques for complying with this requirement include magnetic and optical isolation techniques which are well known in the art. However, such isolation results in an increased susceptibility to radiated noise, especially mains or line frequency noise. The electrical potential of the patient is not tied to earth ground and therefore "floats" at the average potential of the electric field surrounding the patient. The floating nature of the patient potential results in a large common mode voltage with respect to earth ground as indicated by the noise voltage source $V_{noise}$ on FIG. 1B. It is desirable to design the medical isolation amplification circuit 100 to reject this common mode voltage to the best possible extent. If this common mode is not sufficiently rejected, line/mains frequency noise is amplified or processed by the medical isolation amplification circuit 100 and therefore appears at one or several signal output(s) of the isolation amplification circuit 100—making meaningful interpretation of the output signals difficult or impossible. The presence of line frequency noise in the output signal(s) of the isolation amplification circuit 100 is a serious problem that can result in misdiagnosis of the patient and/or inappropriate therapy provided to the patient.

As schematically illustrated on FIG. 1A, a power line field (either 120V/60 Hz or 230V/50 Hz or the local voltage and frequency) impinges on the patient causing the electrical potential of the patient to float towards that field potential. The patient is electrically connected to an input stage circuitry 102 of the medical isolation amplification circuit 100 which isolates the patient from earth ground to which the control circuitry stage 103 is referenced using an optical and/or magnetic isolation barrier 105 or similar techniques.

Figure 1B:
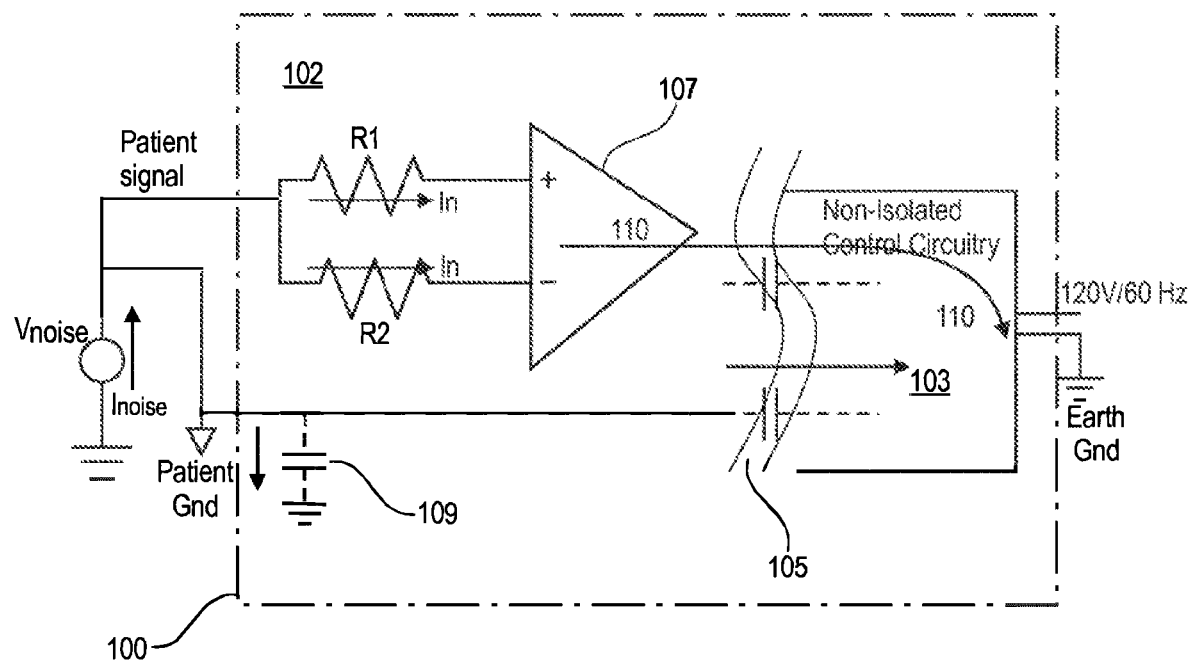
FIG. 1B shows a block diagram of an input-stage circuitry of the medical isolation amplification circuit.

However, a small leakage current still flows from the patient through the isolation amplification circuit 100 to earth ground through the parasitic capacitance, schematically indicated by a first parasitic capacitor 108, across the power supplies and data isolators, and through a parasitic capacitance, schematically indicated by a second parasitic capacitor 109, between the circuit boards and enclosure and ground. The parasitic capacitors 108, 109 are not real components but are rather formed by physical separation of two conductors at different electrical potentials by an insulator. In medical grade amplifiers, the capacitance of a parasitic capacitor is typically in the range of 100 pF. FIG. 1B shows how the current I10 flowing across the isolation barrier 105 becomes a differential voltage which the input stage circuitry 102 cannot reject. A noise current Inoise flows from the noise source Vnoise through the patient cable. Most of the noise current Inoise may flow directly to patient ground from the previously discussed patient ground electrode, but respective noise current component, In, flows through input resistors R1 and R2 of the input stage circuitry 102. These noise currents, In, cross the isolation barrier 105 from the control circuitry stage 103 of the medical isolation amplification circuit 100. The voltage generated across these resistors is:

$$V_{R1}=In*R1 \text{ and}$$

$$V_{R2}=In*R2$$

This generates a differential voltage across non-inverting and inverting inputs of the operational or differential amplifier 107 of:

$$\begin{aligned}V_{diff} &= (V_{noise} - V_{R1}) - (V_{noise} - V_{R2})\\&= -V_{R1} + V_{R2}\\&= -\text{In}^*R1 + \text{In}^*R2\\&= \text{In}^*(R2 - R1)\end{aligned}$$

Consequently, any slight differences, or mismatches, of impedance or resistance between R1 and R2 will result in a differential voltage appearing across the non-inverting input (+) and inverting input (−) of the operational or differential amplifier 107. This differential voltage will be amplified and/or buffered by the differential amplifier 107, carried across the isolation barrier 105 as an error or noise voltage/current signal 110, and therefore finally appearing in the output signal or signal(s) of the medical isolation amplification circuit 100.

Figure 2:
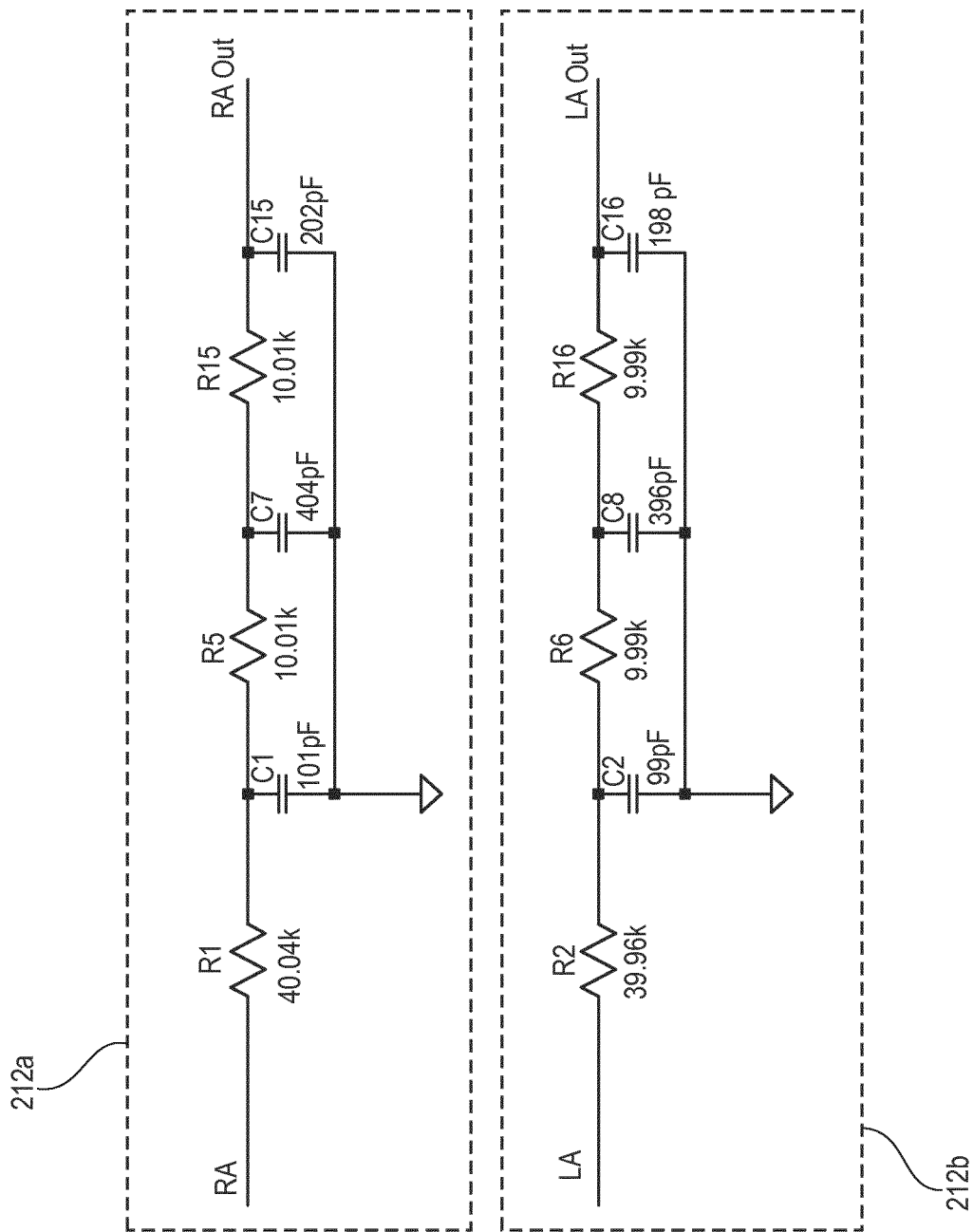
FIG. 2 shows a schematic circuit diagram of first and second filter networks of the input-stage circuitry of the medical isolation amplification circuit.

The skilled person will understand that the resistance of R1 and R2 illustrated on FIG. 1B in practice may form part of the respective input filter networks of the first and second input channels of the input stage circuitry 102. FIG. 2 shows a first and second prior art filter networks, 212a, 212b, of the input stage circuitry 102. The first input filter network 212a or input channel may be connected to an electrode on the Right Arm (RA) and the second input filter network or channel 212b may be connected to an electrode on the Left Arm (LA). RA Out and LA Out, which are the respective output signals of the first and second input filter networks 212a, 212b may be connected directly to the previously discussed non-inverting input (+) and inverting input (−) of the operational or differential amplifier 107. The passive components of each of the first and second filter networks like resistors R1, R2, R3, R4, and capacitors C1, C2, C3 and C4 etc. may be configured to form respective lowpass filters for lowpass filtering the first and second electrical signals provided by the RA and LA electrodes. The corresponding resistors and capacitors in the first and second input filter networks, e.g. R1 and R2 or C1 and C2, will normally be chosen to nominally match each other, but are illustrated as possessing slightly different resistance or capacitance values due to manufacturing tolerances. Hence, the difference or mismatch in impedance between the first and second filter networks 212a, 212b leads to the previously discussed problems with insufficient suppression of the common mode voltage appearing at the first and second electrical input signals at RA and RB.

Figure 3:
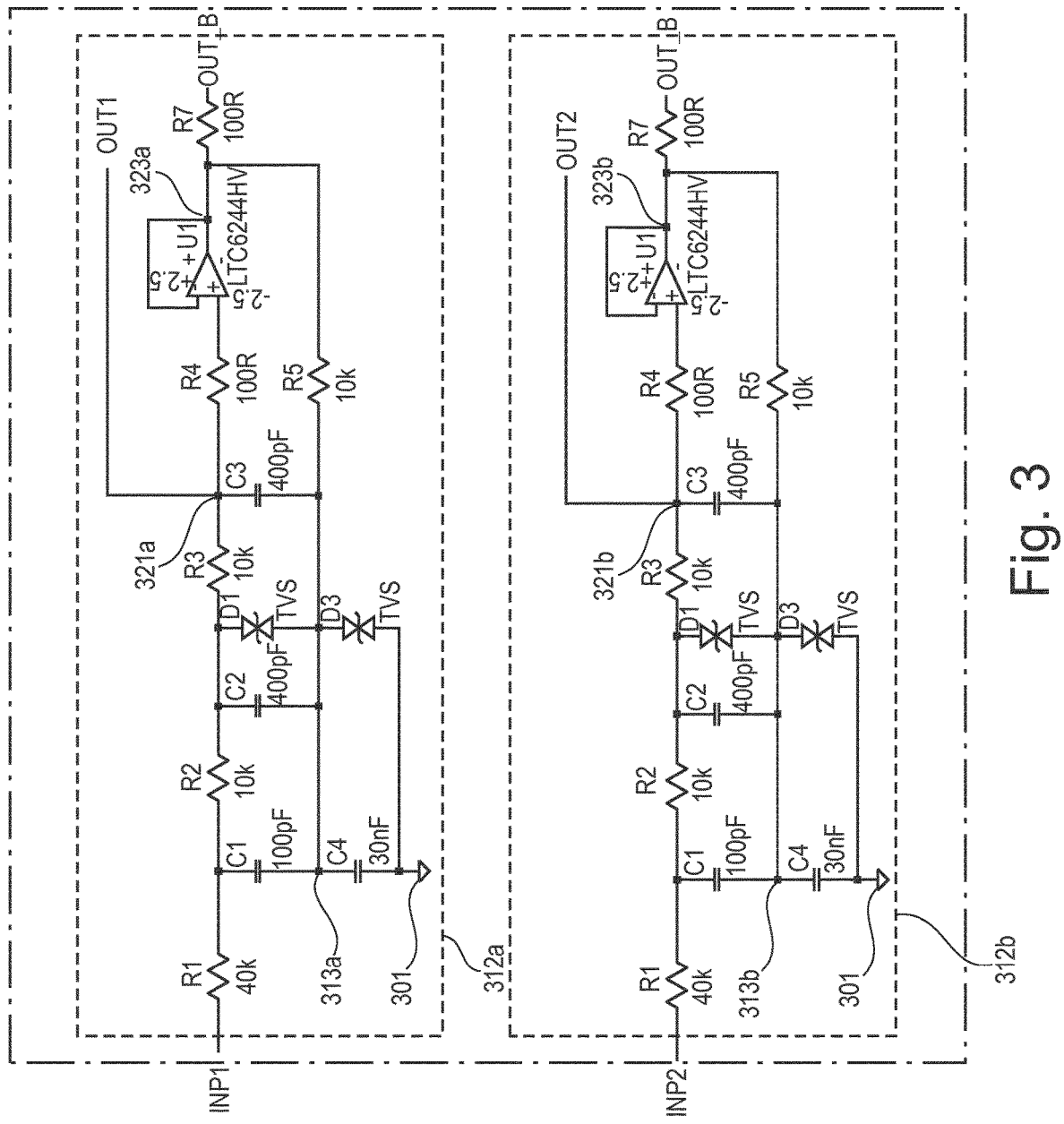
FIG. 3 shows a schematic circuit diagram of first and second exemplary filter networks of the input-stage circuitry of an medical isolation amplification circuit in accordance with a first embodiment of the invention.

FIG. 3 shows a simplified circuit diagram 300 of first and second filter networks, 312a, 312b, of an input stage circuitry of an isolation amplification circuit, for example for medical applications, in accordance with a first embodiment of the invention. The corresponding components in the first and second filter networks 312a, 312b or input filter networks have been given the same names for convenience and these corresponding components are preferably chosen to nominally match each other as illustrated on the circuit diagram. However, the skilled person will understand that such nominally matching components in a practical circuit construction will possess slightly different resistance or capacitance values due to manufacturing tolerances, drift ageing etc.

Figure 4:
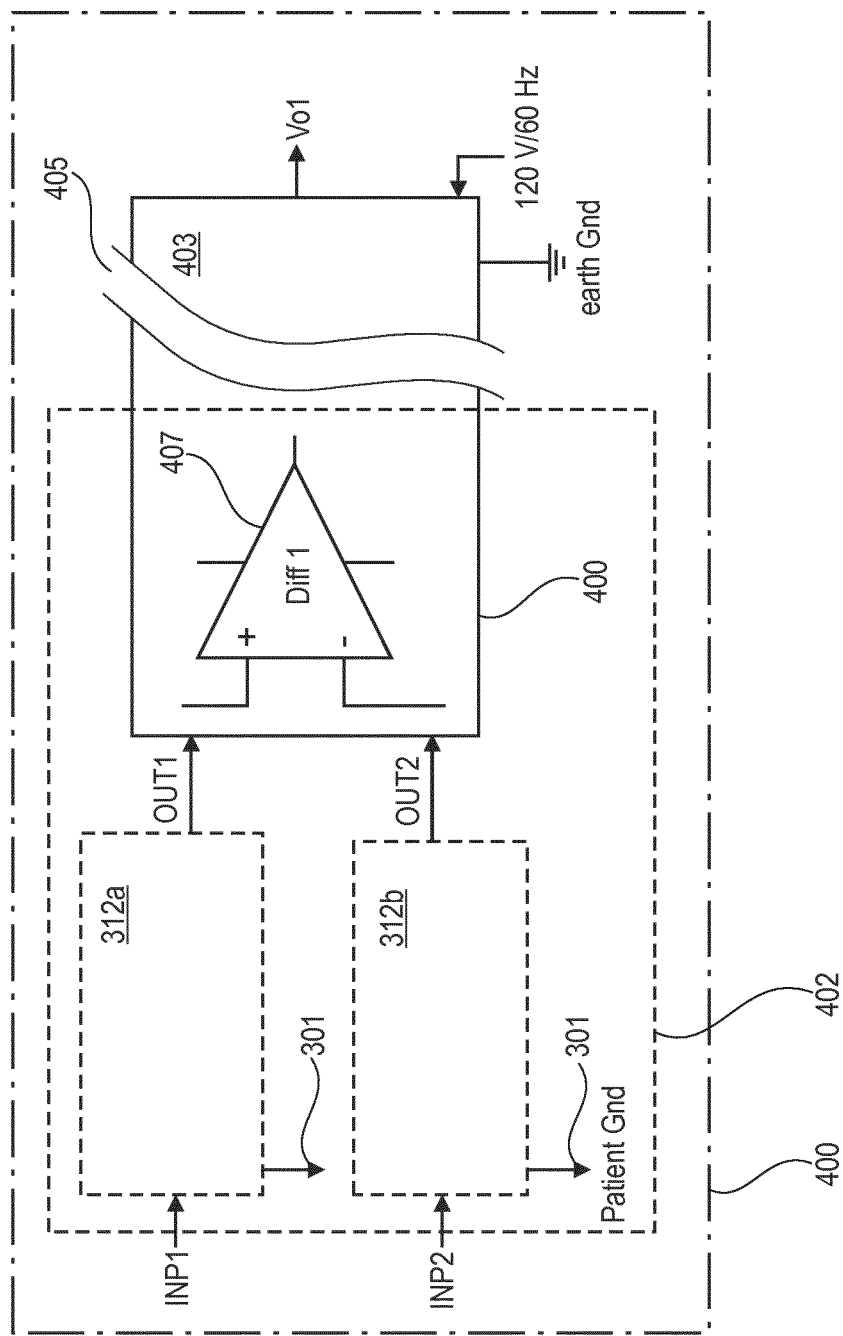
FIG. 4 shows a simplified schematic block diagram of the medical isolation amplification circuit comprising the first and second exemplary filter networks of the input-stage circuitry.

FIG. 4 shows a simplified block diagram of an exemplary isolation amplification circuit 400 incorporating the first and second filter networks 312a, 312b in accordance with a first embodiment of the invention. The first and second filter networks or circuits, 312a, 312b use respective negative feedback paths or loops to minimize respective currents flowing through the first and second filter networks at low frequencies—for example frequencies below 500 Hz. The feedback loop may be unconditionally stable if it is configured with a return gain less than unity. A significant advantage of these feedback paths is a reduction of the currents flowing from the first and second input nodes INP1, INP2 through the first and second filter networks 312a, 312b. Since, at low frequencies such as below 2 kHz or 1 kHz, there is almost no current flowing through the first and second filter networks and any difference or mismatch in values of the passive filter components does not result in a differential voltage between the respective output voltages, OUT1, OUT2 of the first and second filter networks 312a, 312b.

With reference to FIG. 3, the first filter network 312a comprises a first input node, INP1, a first output node OUT1 and a first common node 313a to which the respective negative terminals of the parallelly arranged passive components, C1, C2, D1, C3 of the first filter network, are connected. The second filter network 312b comprises same input, outputs and passive components. The skilled person will understand that each of the first and second filter networks 312a, 312b preferably comprises a single-pole or multi-pole lowpass filter inserted between the first or second input node, INP1/2 and the first or second output node OUT1/OUT2. The cut-off frequency of a first pole formed by a first resistor R1 and capacitor C1 may lie between 30 kHz and 50 kHz. The lowpass filtering of the electrical input voltage at INP1 or INP2 is useful for numerous purposes such as attenuating or suppressing Radio-Frequency (RF) voltages/currents delivered to the first input node INP1 by an ablation catheter or other RF sources. The first resistor R1 may have a resistance of about 40 k$\Omega$ as illustrated. In this manner, the first output signal at the first output node OUT1 is generated as a lowpass filtered version of the electrical input signal at INP1 and in a corresponding manner for the second output signal at the second output node OUT2 relative to the electrical input signal at INP2. The skilled person will understand that alternative embodiments of the first and second filter networks 312a, 312b may comprise other types of frequency selective filters such as highpass filters, bandpass filter or band-reject filters instead of the illustrated lowpass filters or in addition to the illustrated lowpass filters.

The skilled person will appreciate that each of the first and second common nodes 313a, 313b of the first and second filter network 312a, 312b in conventional input filter networks would have been connected to the patient ground as readily apparent from FIG. 2. In contrast, in accordance with the present embodiment of the invention, the first common node 313a of the first filter network 312a is coupled to one terminal of C4 for receipt of the first lowpass filtered output signal and the second common node 313b of the second filter network 312b is coupled to one terminal of the other C4 capacitance for receipt of the second lowpass filtered output signal.

The first resistor R1 is optional but may be helpful for medical embodiments of the present isolation amplification circuit (400 of FIG. 4) because the resistance of R1 protects the patient from DC currents flowing out of the first or second filter networks 312a, 312b under single fault conditions. Resistor R1 also limits the input current to the first or second filter network in the case of patient defibrillation that often produces very large transient input voltages at the first and/or second input node INP1, INP2. The resistors R4 and R7 are entirely optional and may be left out in other embodiments of the invention.

In certain embodiments of the isolation amplification circuit the second output node OUT2 is connected to respective inputs of multiple differential amplifiers such that OUT2 is used as a common unipolar reference for the multiple differential amplifiers.

Each of the first and second filter networks 312a, 312b may additionally comprise one or more non-linear element(s) such as voltage limiters to protect the first filter network 312a and other circuits and components of the isolation amplification circuit against harmful transient voltages for example defibrillation associated voltage pulses/ spikes. The present embodiment of the first filter network 312a comprises a first non-linear element in form of a transient-voltage-suppression (TVS) diode D1 connected from the intermediate series node at the junction of series resistors R2 and R3 to the first common node 313a. A second non-linear element in form of another transient-voltage-suppression (TVS) diode D3 is connected from the first common node 313a to patient ground 301. Hence, large transient input voltages appearing at the first input node INP1 and propagating through the first filter network 312a switch the TVS diodes D1, D3 from a normally inactive state to an active or conductive state. In this manner transient voltages and currents are shorted to the patient ground node 301 via a low-impedance conductive path. Since R1 and R2 act as a voltage divider, C1 has not been protected with a TVS. However, in some cases an additional TVS in parallel with C1 may be added.

The first filter network 312a is connected within a first feedback loop or path of the filter network comprising a buffer amplifier U1 and a first feedback lowpass filter that comprises feedback resistor R5 and feedback capacitor C4. The buffer amplifier U1 may comprise a high-impedance unity gain buffer—for example formed around a non-inverting operational amplifier as illustrated. This means that the input signal at the non-inverting input (+) of U2 is essentially identical to the the first output signal at the first output node OUT1 and also identical to the output signal of the buffer amplifier U1 at node 323a. Hence, the first feedback path is configured to supply a lowpass filtered output signal to the first common node 313a via the output of buffer U1 and the feedback resistor R5 and feedback capacitor C4. The cut-off frequency of the first feedback lowpass filter is set by the resistance of R5 and capacitance of C4. The cut-off frequency of the first feedback lowpass filter may be set to a value between 200 Hz and 2 kHz such as between 500 Hz and 1 kHz by appropriate selection of R5 and C4. The cut-off or corner frequency of the first feedback lowpass filter is preferably higher than a desired measurement bandwidth which depends on the characteristics of the first electrical signal. The desired measurement bandwidth may for example be 500 Hz and the cut-off frequency of the first feedback lowpass filter may be set to 1500 Hz. Generally, the CMRR improves with higher cut-off frequency of the first feedback lowpass filter. However, some amplification may occur when the impedance of capacitor C3 decreases while there is insufficient attenuation from the feedback path. This amplification may be removed by a low pass filter (not shown) arranged downstream of the isolation amplification circuit (400 of FIG. 4) to provide the desired signal bandwidth of the first electrical input signal.

The skilled person will appreciate that the working mechanism of the first feedback path relies on the buffer U1 to maintain its output voltage, at node 323a, at the substantially the same voltage as its non-inverting input as discussed above. Hence, at low frequencies, and especially at the power line frequency around 50 Hz or 60 Hz, where an impedance of C4 is large compared to the resistance of R5 by proper selection of these passive components, this mechanism results in the same noise voltage on both sides of C3 and on both sides of each of the other components in the first input network 312a. Hence, there will not flow any noise current through any of the components of the network 312a including through a parasitic capacitance of D1 except across C4. Due to the lack of noise current in the network 312a there will not be generated any substantial noise voltage across the network 312a in response to a (large) common mode voltage at low frequencies at the input INP1.

At higher frequencies, such as above 500 Hz, 1 kHz or 2 kHz, the impedance of C4 is relatively small compared to R5, essentially connecting the first common node 313a, and hence the components C1, C2, C3, D1, of the first filter network 312a to patient ground (301). The electrical input voltage at INP1 is therefore applied across the first filter network 312a to the latter now operates as a single-pole or multipole lowpass filter, as designed. The second filter network 312b works in a corresponding manner to suppress or attenuate the noise voltage across the network 312b in response to a (large) common mode voltage at low frequencies at the second input INP2.

In this manner, small differences in component values of one or more passive and/or active components between the nominally identical first and second filter networks 312a, 312b will not result in a differential voltage between the first and second output signals at the first and second output nodes OUT1, OUT2. Therefore, the first and second filter networks 312a, 312b of the input stage circuitry 402 will not degrade, or at least markedly reduce any degradation of the CMRR of the medical isolation amplification circuit 400.

The skilled person will appreciate that the first feedback path of the first filter network 312a which includes analog circuitry and components like the buffer amplifier U1 and the feedback resistor R5 and feedback capacitor C4 in the alternative may be embodied as digital circuit(s) and digital signal processing algorithms or program code. For example, the first feedback path may comprise a first analog-to-digital converter, a first digital lowpass filter and a first digital-to-analog converter connected between the first output node OUT1 and the first common node 313a to supply the lowpass filtered feedback signal to the latter node. The first digital lowpass filter may have similar frequency response characteristics of that one the above-discussed analog lowpass filter or comprise additional poles for a steeper frequency roll-off. The first digital lowpass filter may be implemented by executable code or hardware of a digital signal processor (DSP) such as a software programmable DSP/microprocessor or a hard-wired DSP. The second feedback path of the second filter network 312b may be designed in a similar way using digital circuits and digital signal processing. In some embodiments of the isolation amplification circuit 400, the DSP is shared between the first and second filter networks 312a, 312b to minimize the number of separate circuits and lower manufacturing and component costs.

In the exemplary isolation amplification circuit 400 illustrated on FIG. 4, the input stage circuitry 402 comprises a differential amplifier 407. An inverting input of the differential amplifier 407 is electrically coupled to the first output signal at OUT 1 of the first filter network 312a and a non-inverting input of the differential amplifier 407 is electrically coupled to the second output signal at OUT2 of the second filter network 312b. The power supply voltage(s) of the differential amplifier 407 is referenced to patient ground 301, since the differential amplifier 407 is arranged in the input stage circuitry 402 of the isolation amplification circuit 400. The isolation amplification circuit 400 also comprises a control circuitry stage 403 which is coupled to the input stage circuitry 402 via an optical and/or magnetic isolation barrier 405. The properties of the optical and/or magnetic isolation barrier 405 may be similar to those discussed above with reference to the prior art isolation amplifiers. One or several patient diagnostic or therapeutic signals, schematically indicated as Vo1, may have been derived from the first and second electrical input signals and transmitted across the galvanic isolation barrier 405 to be supplied at one or several output terminals (not shown) of the isolation amplification circuit 400. Patient diagnostic signals may comprise ECG signals obtained from the patient's body, acting as a signal source, via suitable patient electrodes connected to the first and second input nodes INP1, INP2 of the input stage circuitry 402. Various active digital and/or analog circuits (not shown) of the control circuitry stage 403 may be supplied with power from a DC power supply energized by a mains line comprising at least one voltage phase, e.g. 120V/60 Hz, 230V/50 Hz or a local voltage and frequency, and earth ground as schematically illustrated on the drawing. In alternative embodiments of the invention, the control circuitry stage 403 is powered or energized by a battery supply—for example comprising one or more rechargeable batteries.

The invention claimed is:

1. An isolation amplification circuit comprising:
    an input stage circuitry and a control circuitry stage inter-connected through a galvanic isolation barrier; said input stage circuitry being referenced to a first ground potential and configured to receive at least a first electrical signal and a second electrical signal generated by a signal source;
    said input stage circuitry comprising:
    a first filter network comprising a first input node, a first output node and first common node wherein the first output node is configured to supply a first output signal in response to application of the first electrical signal at the first input node; and
    a second filter network comprising a second input node, a second output node and a second common node, wherein the second output node is configured to supply a second output signal in response to application of the second electrical signal at the second input node; and
    a first feedback loop of the first filter network including a first buffer amplifier with an input coupled to the first output signal of the first filter network and a buffer amplifier output connected to an input of a first low-pass filter of the first feedback loop for supplying a first low-pass filtered feedback signal to the first common node, wherein one or more passive components inside the first feedback loop is connected in series with the input of the first buffer amplifier and one or more passive components inside the first feedback loop is connected between the input of the first buffer amplifier and the first common node; and
    a second feedback loop of the second filter network including a second buffer amplifier with an input coupled to the second output signal of the second filter network and an output connected to an input of a second low-pass filter of the second feedback loop for supplying a second low-pass filtered feedback signal to the second common node.

2. The isolation amplification circuit according to claim 1, wherein the first feedback loop comprises:
    a first analog-to-digital converter, a first digital low-pass filter and a first digital-to-analog converter connected between the first buffer amplifier output and the first common node; and
    the second feedback loop comprises:
    a second analog-to-digital converter, a second digital low-pass filter and a second digital-to-analog converter connected between the second buffer amplifier output and the second common node.

3. The isolation amplification circuit according to claim 2, wherein at least the first digital low-pass filter and the second digital low-pass filter are integrated on a common digital signal processor (DSP) circuit, wherein the DSP circuit is a software programmable DSP programmed according to machine-readable instructions stored on a non-transitory medium or a hard-wired DSP.

4. The isolation amplification circuit according to claim 1, wherein the input stage circuitry further comprises:
    a differential amplifier comprising an inverting input electrically coupled to the first output signal of the first filter network and a non-inverting input electrically coupled to the second output signal of the second filter network to produce an amplified output signal;
    said amplified output signal being coupled to the control circuitry stage through the galvanic isolation barrier.

5. The isolation amplification circuit according to claim 1, wherein the control circuitry stage is connected to a power supply; said power supply being connectable to a mains line; said mains line comprising at least one voltage phase, or a local voltage and frequency, and earth ground.

6. The isolation amplification circuit according to claim 1, wherein the signal source comprises a human or animal body for supplying the first electrical signal as a first electro-physiological signal to the first input node of the first filter network via a first electrode; and
    for supplying the second electrical signal as a second electro-physiological signal to the second input node of the second filter network via a second electrode.

7. The isolation amplification circuit according to claim 1, wherein passive components of the first filter network are nominally identical to corresponding passive components of the second filter network.

8. The isolation amplification circuit according to claim 1, wherein the one or more passive components connected between the input of the first buffer amplifier and the first common node of the first filter network comprises at least one non-linear element; and
    wherein the one or more passive components connected between the input of the second buffer amplifier and the second common node of the second filter network comprises at least one non-linear element.

9. The isolation amplification circuit according to claim 1, wherein the galvanic isolation barrier comprises one or more optical isolation element(s) and/or one or more magnetic isolation elements.

10. A method of suppressing common mode signals of an isolation amplification circuit by minimizing flow of current through a first filter network of the isolation amplification circuit and minimizing flow of current through a second filter network of the isolation amplification circuit, said method comprising steps of:
    a) applying a first electrical signal to a first input node of a first filter network of an input stage circuitry of the isolation amplification circuit,
    b) applying a second electrical signal to a second input node of a second filter network of the input stage circuitry,
    c) generating a first output signal of the first filter network in response to the first electrical signal,
    d) buffering the first output signal via a buffer amplifier to provide a buffered first output signal,
    e) generating a second output signal of the second filter network in response to the second electrical signal,
    f) buffering the second output signal via a buffer amplifier to provide a buffered second output signal,
    g) low-pass filtering the buffered first output signal to generate a first feedback signal,
    h) low-pass filtering the buffered second output signal to generate a second feedback signal, i) applying the first feedback signal to a common node of the first filter network;

j) applying the first feedback signal to a first loop capacitor configured to close the first feedback loop, k) applying the second feedback signal to a common node of the second filter network to close a second feedback loop around the second filter network, and l) applying the second feedback signal to a second loop capacitor configured to close the second feedback loop of the second filter network, wherein one or more passive components inside the first feedback loop is connected in series with an input of the first buffer amplifier, and one or more passive components of the first feedback loop is connected between the input of the first buffer amplifier and the first common node; and wherein one or more passive components inside the second feedback loop is connected in series with an input of the second buffer amplifier, and one or more passive components inside the second feedback loop is connected between the input of the second buffer amplifier and the second common node.

11. The isolation amplification circuit according to claim 9, wherein a cut-off frequency of the low-pass filtering of the first buffered output signal lies between 500 Hz and 1.5 kHz and wherein a cut-off frequency of the low-pass filtering of the second buffered output signal lies between 500 Hz and 1.5 kHz.

12. The isolation amplification circuit according to claim 1, wherein the first feedback loop comprises:

a first feedback capacitor connected from the first common node to the first ground potential and a first feedback resistor connected between the first common node and the buffer amplifier output, a first loop capacitor connected from the first common node to a first junction node for closing the first feedback loop around the one or more passive components connected in series with the input of the first buffer amplifier and around the one or more passive components connected between the input of the first buffer amplifier and the first common node;

wherein the second feedback loop comprises:

a second feedback capacitor connected from the second common node to the first ground potential and a second feedback resistor connected between the second common node and the buffer amplifier, a second loop capacitor connected from the second common node to a second junction node for closing the second feedback loop around the one or more passive components connected in series with the input of the second buffer amplifier and around the one more passive components connected between the input of the second buffer amplifier and the second common node.

13. The isolation amplification circuit according to claim 12, wherein the one or more passive components connected in series with the input of the first buffer amplifier and the one or more passive components connected between the input of the first buffer amplifier and the first common node of the first filter network form at least one of a low-pass filter, high-pass filter, band-pass filter, band-reject filter; and wherein the one or more passive components connected in series with the input of the second buffer amplifier and the one or more passive components connected between the input of the second buffer amplifier and the second common node of the second filter network form at least one of a low-pass filter, high-pass filter, band-pass filter, band-reject filter.

14. The isolation amplification circuit according to claim 12, wherein a cut-off frequency of a low-pass filter formed by the first feedback resistor and first feedback capacitor lies between 200 Hz and 2 kHz, and a cut-off frequency of a low-pass filter formed by the second feedback resistor and second feedback capacitor lies between 200 Hz and 2 kHz.

* * * * *

UNITED STATES PATENT AND TRADEMARK OFFICE
CERTIFICATE OF CORRECTION

PATENT NO. : 11,451,203 B2
APPLICATION NO. : 17/051464
DATED : September 20, 2022
INVENTOR(S) : Wodlinger et al.

It is certified that error appears in the above-identified patent and that said Letters Patent is hereby corrected as shown below:

In the Claims

At Column 14, Line 13 (Claim 12), please delete "around the one more passive components" and insert --around the one or more passive components-- therefor.

Signed and Sealed this
Thirteenth Day of December, 2022

Katherine Kelly Vidal
*Director of the United States Patent and Trademark Office*